United States Patent [19]

Pederson et al.

[11] Patent Number: 4,911,174
[45] Date of Patent: Mar. 27, 1990

[54] METHOD FOR MATCHING THE SENSE LENGTH OF AN IMPEDANCE MEASURING CATHETER TO A VENTRICULAR CHAMBER

[75] Inventors: Brian D. Pederson, St. Paul; Rodney W. Salo, Fridley, both of Minn.

[73] Assignee: Cardiac Pacemakers, Inc., St. Paul, Minn.

[21] Appl. No.: 309,221

[22] Filed: Feb. 13, 1989

[51] Int. Cl.[4] .............................................. A61B 5/02
[52] U.S. Cl. .................................. 128/695; 128/694; 128/734
[58] Field of Search ............... 128/695, 673, 693, 694, 128/734, 419 PG, 419 D, 786, 783, 784, 785

[56] References Cited

U.S. PATENT DOCUMENTS

| | | | |
|---|---|---|---|
| 3,942,536 | 3/1976 | Mirowski et al. | 128/786 |
| 4,291,699 | 9/1981 | Geddes et al. | 128/419 D |
| 4,380,237 | 4/1983 | Newbower | 128/693 |
| 4,587,975 | 5/1986 | Salo et al. | 128/693 |
| 4,674,518 | 6/1987 | Salo | 128/695 |
| 4,840,182 | 6/1989 | Carlson | 128/694 |

FOREIGN PATENT DOCUMENTS 2471177 6/1981 France .................................. 128/693

Primary Examiner—Lee S. Cohen
Assistant Examiner—Kennedy J. Schaetzle
Attorney, Agent, or Firm—Haugen and Nikolai

[57] ABSTRACT

A method for matching the distance spanned by a plurality of surface electrodes on an impedance measuring catheter to the size of a ventricular chamber to be measured is disclosed. The catheter includes a plurality of longitudinally spaced electrodes extending from its distal end and spanning a distance known to be greater than the maximum length of a ventricular chamber. With the distal end of the catheter located at the apex of the ventricle, an AC drive signal is applied between the distal electrode and a proximal electrode known to be outside of the ventricle. By then sensing the resulting voltage between successive adjacent electrode pairs and comparing same, the pair where a different characteristic is exhibited is known to be at the transition between the ventricle and the atrium.

7 Claims, 4 Drawing Sheets

METHOD FOR MATCHING THE SENSE LENGTH OF AN IMPEDANCE MEASURING CATHETER TO A VENTRICULAR CHAMBER

BACKGROUND OF THE INVENTION

I. Field of the Invention

This invention relates generally to a system for measuring the ventricular volume of a human or animal heart by using impedance plethysmography and more particularly to a method for matching the sensed length of the impedance catheter to the length dimension of the ventricle.

II. Discussion of the Prior Art

In the Salo U.S. Pat. No. 4,674,518, which is assigned to the assignee of the present invention, there is described a method and apparatus for making instantaneous measurements of the ventricular volume by utilizing an intracavity electrical impedance catheter. That catheter comprises a tubular sheath having a plurality of spaced surface electrodes (ring electrodes) disposed sufficiently near the distal end of the catheter so that those electrodes effectively span the length dimension of the chamber whose volume is to be measured. To obtain accurate measurements of ventricular volume, it is imperative that one be able to locate the particular pair of sensing electrodes located at the transition between the ventricular chamber and the atrium or aorta, depending upon which ventricular chamber is involved. When this has been accomplished, the volume between each of the electrode pairs may be computed from measured impedance signals and then these volumes may be summed to yield the total ventricular volume. Because there is large variability in the length of the left (and right) ventricle over the total patient population, some means must be provided for matching the total distance spanned by the surface ring electrodes on the catheter to the length of the ventricle being measured.

The aforereferenced Salo U.S. Pat. No. 4,674,518 references the published work of Jan Baan of the Netherlands. In the work leading to those publications, a number of catheters with electrodes of different spacing were manufactured and the appropriate catheter selected under fluoroscopy. Since the length of the ventricle cannot be accurately estimated without actually introducing a catheter into the chamber, this technique often required the introduction of more than one catheter. Either a measuring catheter with radio opaque markers is positioned in the chamber first and the desired catheter length determined under fluoroscopy or else one of the impedance catheters is introduced and later replaced if it proves to be of the wrong length.

Such a trial and error approach at determining appropriate catheter length is not only time consuming but increases the risk of damage to the blood vessels through which the catheter is routed in achieving placement in the ventricle.

OBJECTS

It is accordingly a principal object of the present invention to provide a novel method for matching the sense length of an impedance catheter to the length dimension of the ventricular chamber whose volume is to be measured.

Another object of the invention is to provide a method of sizing a ventricular impedance measuring catheter to obviate the need for trial and error replacements.

Yet another object of the invention is to provide a method of matching the impedance catheter sensed length to a ventricular dimension so that the same catheter can be used with patients having marked differences in ventricular length.

SUMMARY OF THE INVENTION

In accordance with the present invention, the tubular catheter in question includes a sufficient number of surface electrodes guaranteeing that the total sense length, i.e., the distance between the most distal sense ring and the most proximal sense ring will span the largest of ventricles. Such a catheter may then be used in smaller hearts by determining which sense ring pairs are in the heart chamber and then using only those ring pairs in the computation of the total ventricular volume. In accordance with one technique, an alternating, constant-current voltage signal is applied between the most distal one and a predetermined more proximal one of the plurality of electrodes, the more proximal one being known to fall outside of the ventricular chamber. With such a signal applied, the signals existing between adjacent pairs of sense electrodes located between the driven electrodes are compared. The location of the particular pair of electrodes where the characteristics of the signal therebetween differ from the characteristics of the signals between more distal ones of adjacent pairs of electrodes mark the transition between the ventricle and its associated atrial chamber.

DESCRIPTION OF THE DRAWINGS

Further objects, advantages and features of the invention will become apparent to those skilled in the art from the following detailed description of the preferred method, especially when considered in conjunction with the accompanying drawings in which.

DESCRIPTION OF THE PREFERRED EMBODIMENT

Figure 1:
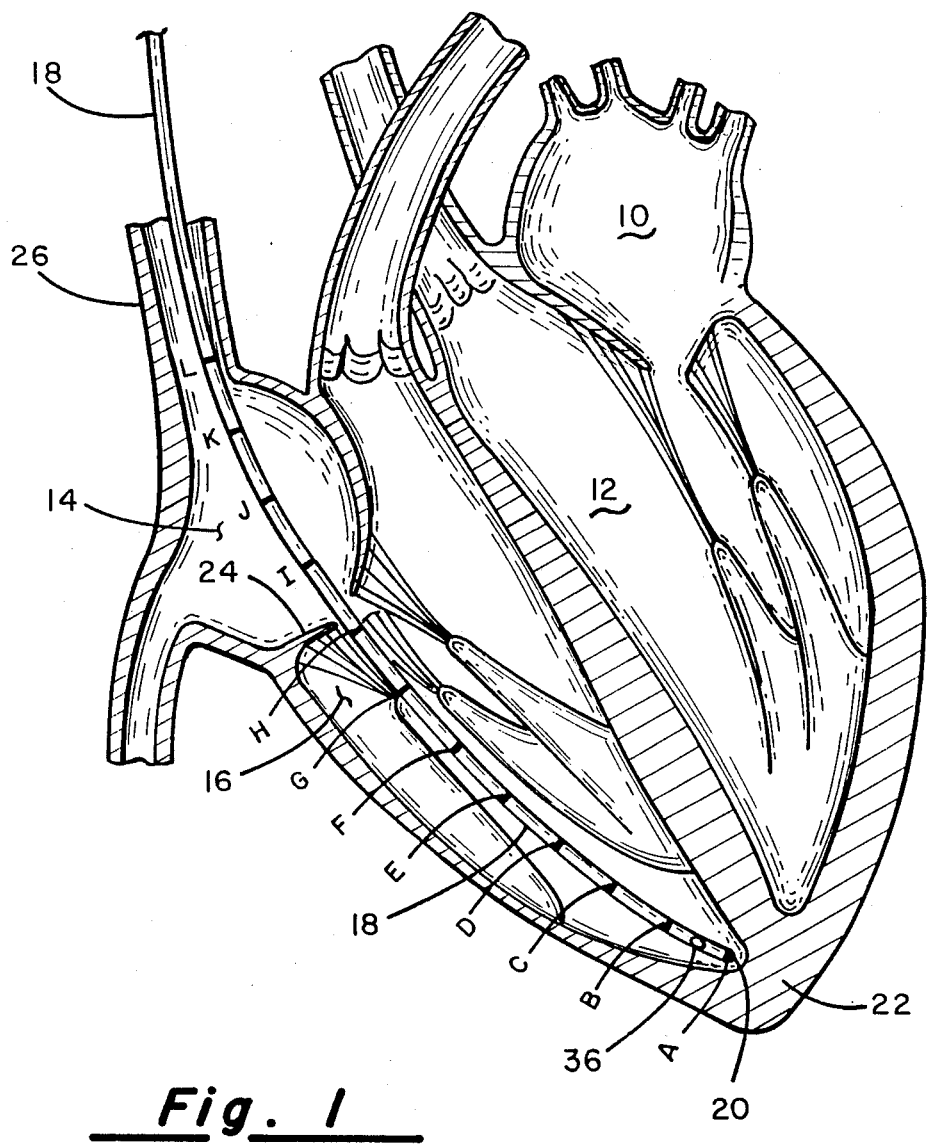
FIG. 1 illustrates an impedance measuring catheter located in a heart.

Referring to FIG. 1, t here is shown a longitudinal section of the heart. The left atrium and left ventricle are identified by numerals 10 and 12, respectively, and the right atrium and right ventricle are identified by numerals 14 and 16. Shown located in the right ventricle is an impedance measuring catheter 18 whose distal tip electrode 20 is disposed at the apex 22 of the heart. The catheter 18 passes through the tricuspid valve 24 and through the right atrium 14 exiting the superior vena cava 26. The distal end portion of the catheter 18 is provided with a plurality of surface electrodes which are labeled alphabetically from A through L for ease of reference. These surface electrodes may be conductive rings and extending through the lumen of the tubular catheter 18 are the electrical leads (not shown) for conductively connecting each of the electrodes A through L individually to an electronics module adapted to be coupled to the proximal end of the catheter 18 exterior to the body. The electronics module includes switching means which allow a relatively high frequency, constant current sinusoidal voltage to be applied across predetermined ones of the plural electrodes. In a typical application, the sinusoidal driving signal may be applied across the distal tip electrode A and the most proximal electrode L.

It should also be mentioned at this point that the length of the catheter spanned by the surface electrodes exceeds the maximum ventricular chamber length dimension which one would expect to encounter. Thus, if the catheter 18 were to be used with a pediatric patient, perhaps only surface electrodes A through F would reside in the right ventricle of a young heart. With an adult heart, however, such as illustrated in FIG. 1, surface electrodes A through H clearly reside in the right ventricle.

To avoid the necessity of fluoroscopic exam with a measuring catheter or trial and error substitution of impedance measuring catheters of differing numbers of sense electrodes until one fitting the heart in question is arrived at, in accordance with the present invention, additional surface electrodes are included on the impedance catheter so that the total sense length (the distance between the most distal sense ring and the most proximal sense ring) will more than span the largest of ventricles. Then, when using the same catheter configuration in smaller hearts, a determination is made as to which sense ring pairs are in the ventricular chamber and then only those ring pairs are utilized in the computation of the total ventricular volume. For example, in carrying out the present invention, a catheter having a ring spacing of 0.5 centimeters between electrodes A and B, and 1.0 centimeter spacings between the remaining electrodes B to C ... K to L, the distance from the distal tip 20 to the most proximal sense electrode K can be varied from 4.0 centimeters to 8.0 centimeters as different combinations of electrodes are selected. As such, this single catheter can accommodate patients with very small hearts and very large hearts.

Referring next to the schematic diagram of FIGS. 2 and 3, one technique used to identify and select those electrodes which are in the particular patient's ventricle will be explained. A source of a constant current alternating voltage 28 is schematically illustrated as being connected between the distal electrode A and the most proximal electrode L. It is to be understood that this a schematic showing in that the signals would actually be applied to conductive leads running through the lumen or wall of the catheter body 18 from its proximal end and terminating at the appropriate electrodes. Likewise, a series of sense amplifiers 30, 32 and 34 have their inputs connected across adjacent pairs of sense electrodes. Specifically, amplifier 30 is shown as having its inputs coupled across surface electrodes B and C, sense amplifier 32 having its inputs coupled across surface electrodes C and D and sense amplifier 34 with its inputs coupled across electrode pair D and E. With the voltage source 28 operational, and with the patient's heart beating, a time varying voltage signal will be developed at the output of each of the amplifiers as illustrated. As is explained in the Salo U.S. Pat. No. 4,674,518 previously cited, the output signals are directly proportional to the instantaneous impedance measured between the adjacent electrode pairs. In that the wave shape of the output signals from each of the sense amplifiers 30, 32 and 34 are of comparable phase and morphology, it is known that even the most proximal pair of electrodes, D and E, reside in the ventricle.

Figure 2:
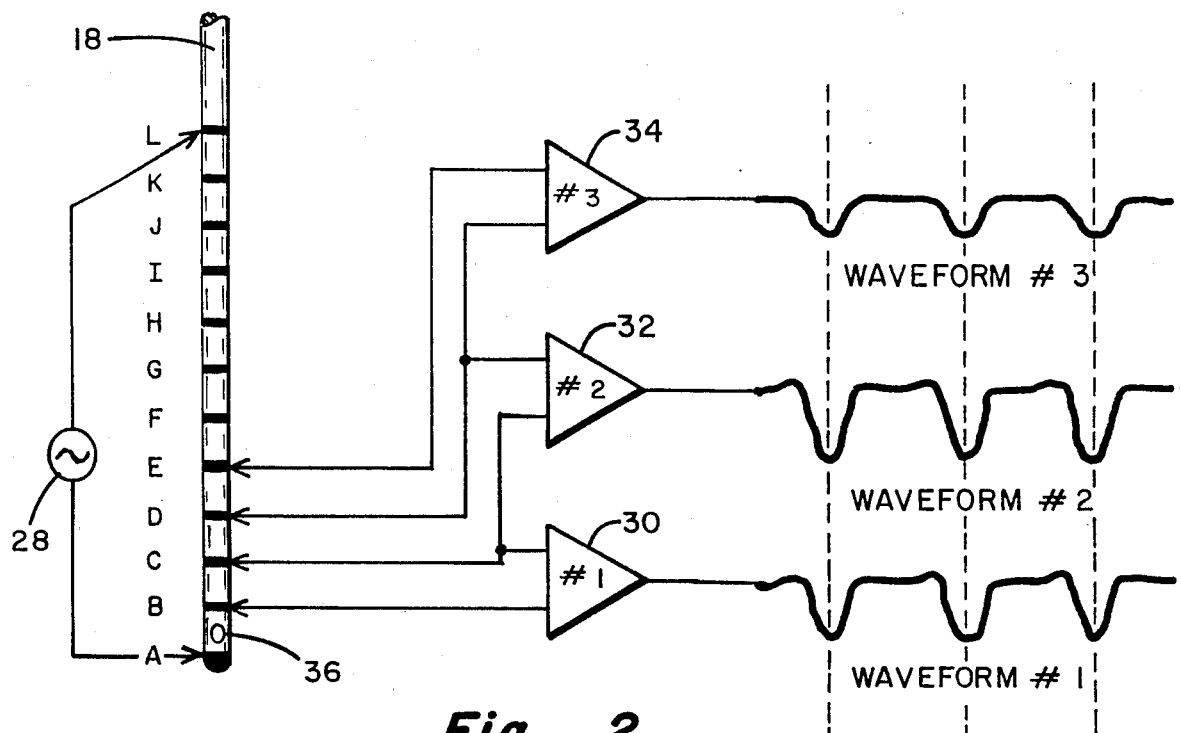
FIG. 2 shows the same catheter arrangement as in FIG. 1 in a schematic fashion to better illustrate the principles of the invention.
Figure 3:
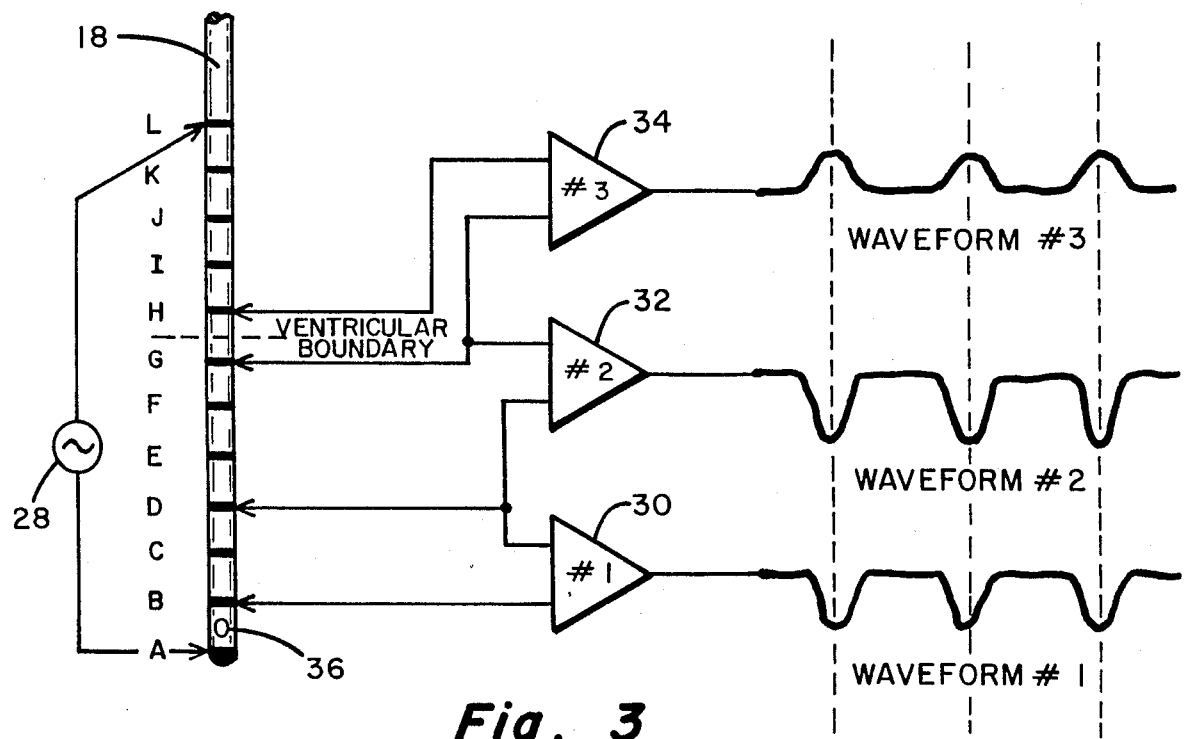
FIG. 3 is a further schematic diagram helpful in understanding the method of the present invention.

Referring now to FIG. 3, there is illustrated a setup similar to FIG. 2 except that sense amplifier no. 3 has been switched so as to be connected across a more proximal electrode pair G and H. The outputs from sense amplifiers 30 and 32 still exhibit a similar phase and shape pattern, reflecting that the electrode pairs with which those two amplifiers are coupled still reside in the ventricle. It should be further noted, however, that the output from the most proximal sense amplifier 34 has a different phase relationship from the signals obtained at the outputs from sense amplifiers 30 and 32. In that sense amplifier 34 and sense amplifier 32 share a common surface electrode G, it is known that the ventricular boundary, i.e., the transition between the right ventricle and the right atrium falls between the two surface electrodes G and H.

Summarizing, then, one technique for locating the most proximal surface electrode still residing in a ventricle of unknown dimension is to use the catheter of FIG. 1 positioned in the ventricular chamber whose volume is to be measured and then selecting the smallest, closest electrode spacing on the catheter. In FIG. 2, this corresponds to connecting electrodes B and C to amplifier 30, C and D to amplifier 32 and D and E to amplifier 34, via an appropriate switching means (not shown). Next, the impedance waveforms from the most proximal electrode pair (electrodes D and E) are compared to the signals from the more distal electrodes. If all of the signals exhibit the same phase relationship and a fairly similar morphology, it is known that all three electrode pairs reside in the ventricle. Next, via the aforementioned switching means, amplifier 34 is successively "walked" up the catheter and at each step the output from the sense amplifier 34 is compared to the others until the waveform for the most proximal selected ring pair no longer matches the other two waveforms. At this point, it is known that both rings of the most proximal ring pair no longer reside in the ventricle. It is also apparent, then, that the surface electrode or rings which remain in the ventricle have been identified.

To avoid the necessity of switching electrode pair outputs to one or more of the sense amplifiers 30, 32 and 34, an alternative approach is to tie each electrode pair to its own sense amplifier. Then, when all of the output waveforms are compared to the most distal one or two waveforms, the location of the transition between the ventricle and the atrium is identified. The surface electrodes then identified as being located within the ventricle can be used in performing the ventricular volume measurement.

Another approach to identifying the sense length of the ventricular chamber to be measured is to compute the covariance between the reference signals (i.e., those signals from the distal ring pairs) and the signals from more proximal ring pairs. The covariance or cross-correlation between two measurements, x and y, is defined by:

$$\sigma_{xy} = \rho_{xy}/\sigma_x\sigma_y$$

where $\rho_{xy}$ = correlation coefficient between x and y $\sigma_x, \sigma_y$ = standard deviations of x and y A covariance less than some empirically determined threshold would be taken to indicate that the proximal waveform differs too much from the reference waveforms and that ring pair would be determined to be outside of the ventricle. Investigations have shown that a covariance of approximately 0.2 can be used as a threshold.

Alternatively, the signals from the several electrode pairs may be compared to another physiological signal which is indicative of ventricular contraction (i.e., ventricular pressure). The phase relationship between an impedance signal and the other indicator will be different outside of the ventricle as opposed to within the ventricle. Since the distal electrode pairs are assumed to be within the ventricle, the most distal electrode pair which shows a new phase relationship will define the ventricular boundary. To obtain a pressure measurement, the catheter 18 is provided with a pressure sensing port 36 communicating with a lumen which is filled with an appropriate fluid such that pressure variations in the ventricle are transmitted to a suitable pressure transducer located at the proximal end of the catheter 18.

Figure 4:
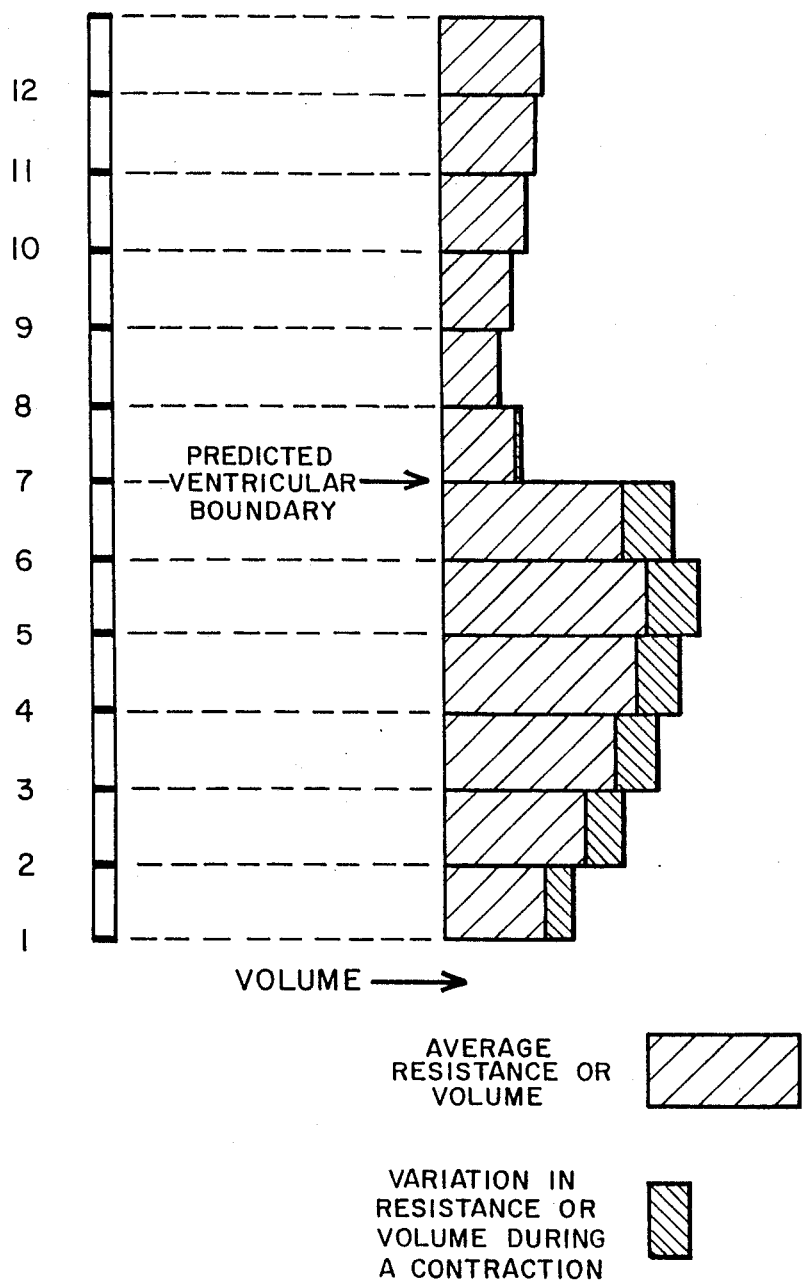
FIG. 4 is a further schematic drawings illustrative of the invention.

Referring next to FIG. 4, a still further approach for identifying the transition or ventricular boundary is to compute the average resistance or volume and the variation in each of these values measured between each electrode pair, from most distal to most proximal, on the catheter 18. As is illustrated in FIG. 4, a fairly dramatic transition in average volume occurs at the boundary. A plot of average resistance would show the opposite relationship to that for volume illustrated in FIG. 4, since volume is inversely proportional to resistance. In addition, the resistance (or volume) changes during contraction are smaller in the right atrium than in the right ventricle. An even more pronounced difference in the extent of resistance or volume changes during contraction occurs when the catheter is positioned in the left ventricle with a portion thereof extending into the aorta.

Figure 5:
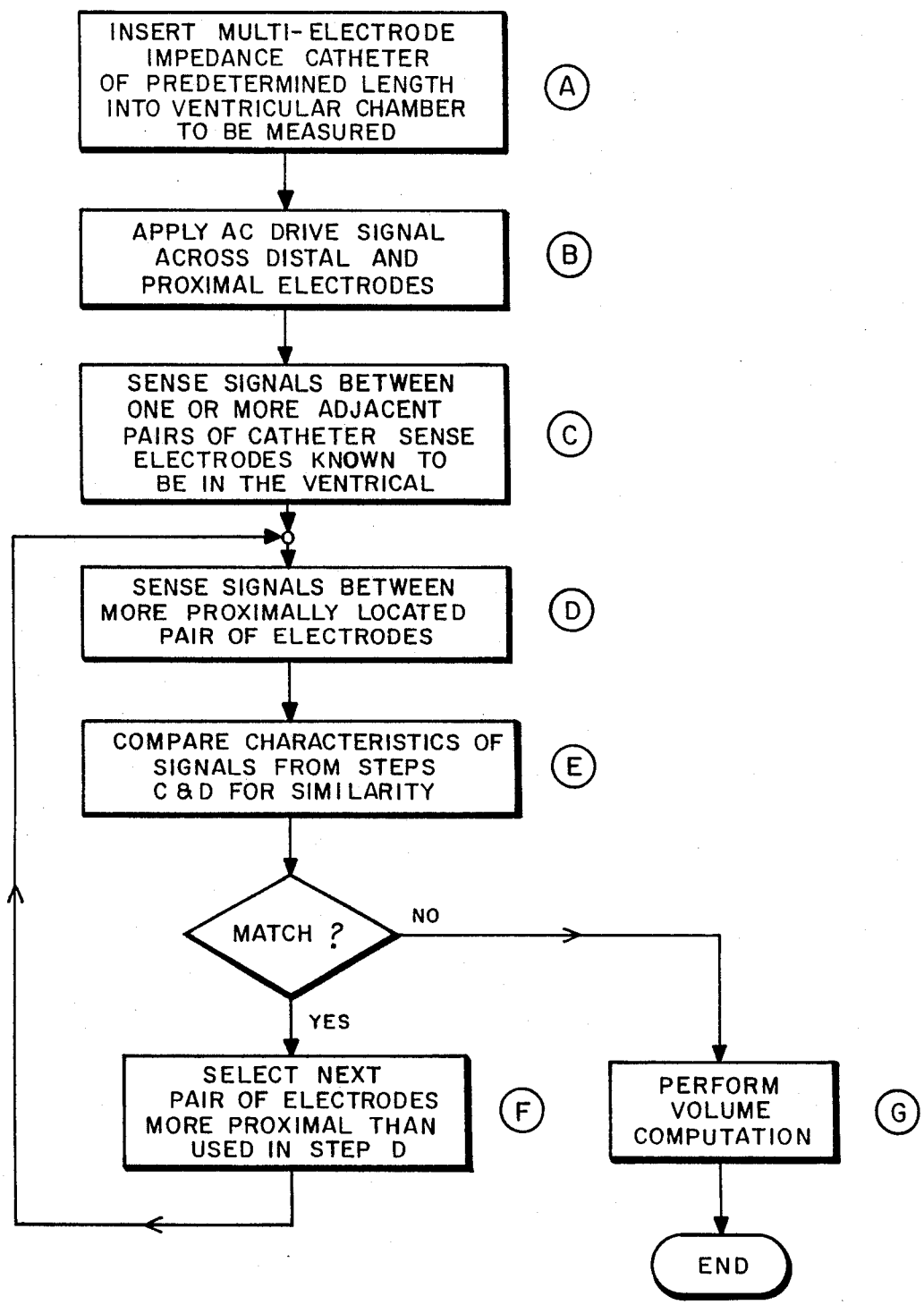
FIG. 5 is a flow diagram illustrating the steps of the method of the present invention.

To more clearly explain the method of the present invention, reference is next made to the method or process flow diagram of FIG. 5. As indicated in the flow diagram of FIG. 5, the first step in the method of the present invention for matching the sense length of an intracardiac impedance catheter to the actual dimensions of a ventricular chamber (step A) includes providing a multi-electrode impedance catheter of the type described herein and inserting same into the ventricular chamber to be measured such that the spaced surface electrodes thereon span a distance known in advance to be greater than the expected length dimension of the ventricular chamber of an adult male. That catheter is routed through the patient's vascular system in a known fashion in such a way that the distal end of the catheter resides in the apex of the ventricular chamber whose volume is to be subsequently measured.

In accordance with step B, an alternating, constant-current, voltage signal is applied between the most distal one and a predetermined more proximal one of the plurality of surface electrodes, the more proximal electrode chosen being known to fall outside of the ventricular chamber in question.

In step C, voltage signals appearing between one or more adjacent pairs of sense electrodes located sufficiently distal so as to be known to be in the ventricle are sensed. Such signals are due to the near field effects caused by the application of the drive signal in step B.

At the same time that step C is carried out, further signals developed between a more proximally located pair of electrodes is sensed. The signals sensed in steps C and D are compared in terms of phase and morphology (step E) and then a determination is made as to whether such comparison results in a match.

If a match condition prevails, it is established that the proximally located pair of electrodes used in step D fall within the ventricular chamber. Step F is then carried out whereby a next pair of electrodes more proximal than those previously used in carrying out step D are selected and steps D, E and F are repeated until the "MATCH-?" test fails. With the particular pair of more proximal electrodes resulting in signals of differing characteristics from those across surface electrodes known to be in the ventricle established, the impedance plethysmography method of measuring the ventricular volume can be carried out using only those sense electrodes determined by the present invention to be resident in the ventricular chamber in question.

As already mentioned, the algorithm set forth in the flow chart of FIG. 5 is only one particular way of identifying the sense length of an impedance measuring catheter disposed within a ventricle. Another method already described includes the use of a separate sense amplifier for each adjacent pair of surface electrodes and then observing the outputs from all of the sense amplifiers to note the one whose output differs from the more distal pairs. A still further method involves determining the covariance between distally located surface electrodes known to be in the ventricle and more proximal electrodes whose location relative to the ventricle is uncertain to determine if the covariance exceeds a pre-established threshold valve.

Moreover, the impedance sensing technique with electrodes known to be in the ventricle can be compared in phase to another ventricular physiologic signal related to chamber mechanics, such as ventricular pressure. Then, when more proximal impedance measurements are taken and compared in phase to the intraventricular pressure, the location where a phase change is noted is indicative of the ventricular boundary.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for matching the sense length of an intracardiac impedance catheter to the dimensions of a ventricular chamber, comprising the steps of:
    (a) providing an elongated, flexible, plastic endocardial catheter having a plurality of spaced surface electrodes extending longitudinally and proximally from a distal end of said catheter so as to span a distance known in advance to be greater than an expected length dimension of an adult ventricular chamber;
    (b) routing said catheter through a patient's vascular system such that said distal end resides in the apex of one ventricular chamber;

(c) applying an alternating, constant-current, voltage signal between a most distal one and a predetermined more proximal one of said plurality of electrodes known to be outside of said ventricular chamber;

(d) sensing signal characteristics existing between adjacent pairs of said electrodes located between said most distal one and said predetermined more proximal one of said plurality of electrodes due to said alternating current applied in step (c);

(e) comparing the characteristics of the signals sensed in step (d) with one another for similarity;

(f) identifying the location of a particular pair of electrodes where the characteristics of the signal therebetween differ from the characteristics of the signals between more distal ones of said adjacent pairs of electrodes.

2. The method as in claim 1 wherein said characteristics being compared include morphology and phase.

3. The method as in claim 1 wherein morphology and phase comparisons are made between electrode signals and an independently derived signal indicative of chamber mechanics.

4. The method as in claim 3 wherein said signal indicative of chamber mechanics is the pressure within said one ventricular chamber.

5. The method as in claim 1 wherein said characteristics compared is the average resistance between said adjacent pairs of said surface electrodes.

6. The method as in claim 1 wherein the said characteristics compared is the change in average resistance between said adjacent pairs of said surface electrodes.

7. A method for matching the sensing length of an intracardiac impedance catheter to the dimensions of a ventricular chamber, comprising the steps of:

(a) providing an elongated, flexible, plastic endocardial catheter having a plurality of spaced surface electrodes extending longitudinally and proximally from a distal end of said catheter so as to span a distance known in advance to be greater than an expected length dimension of an adult ventricular chamber;

(b) routing said catheter through a patient's vascular system such that said distal end resides in the apex of one ventricular chamber;

(c) applying an alternating constant current voltage signal between a most distal one and a predetermined more proximal one of said plurality of electrodes known to be outside said one ventricular chamber;

(d) sensing signal characteristics existing between one or more adjacent pair of said electrodes known to be located in said ventricular chamber, the sensed signal being due to said alternating current applied in step (c);

(e) selecting a further adjacent pair of electrodes more proximal than said one or more adjacent pair of electrodes;

(f) sensing signal characteristics existing between said further adjacent pair of said electrodes;

(g) comparing the characteristics of said signals sensed in step (d) with the characteristics of said signal sensed in step (f) for a match condition;

(h) selecting a further adjacent pair of electrodes even more proximal than the electrodes used in step (f);

(i) repeating steps (f), (g) and (h) until the signal sensed in step (f) differs in said characteristics from the signals sensed in step (d).

* * * * *